United States Patent [19]

Neti et al.

[11] 4,118,193

[45] Oct. 3, 1978

[54] CATALYTIC REACTOR SYSTEMS METHOD AND APPARATUS

[75] Inventors: Radhakrishna Murty Neti, Brea; Kenneth Bruno Sawa, Yorba Linda, both of Calif.

[73] Assignee: Beckman Instruments, Inc., Fullerton, Calif.

[21] Appl. No.: 820,481

[22] Filed: Jul. 29, 1977

[51] Int. Cl.² .............................................. G01N 31/12
[52] U.S. Cl. ........................................ 422/94; 422/54
[58] Field of Search ............ 23/232 R, 232 E, 254 R, 23/254 E, 230 PC, 253 PC

[56] References Cited

U.S. PATENT DOCUMENTS

| | | | |
|---|---|---|---|
| 2,849,291 | 8/1958 | Allison et al. | 23/232 R |
| 3,647,387 | 3/1972 | Benson et al. | 23/230 PC X |

Primary Examiner—Robert M. Reese
Attorney, Agent, or Firm—R. J. Steinmeyer; P. R. Harder

[57] ABSTRACT

An improved catalytic reactor system and method for removing interferents such as reactive hydrocarbons from the gas being sampled by gas component determination apparatus is disclosed. The sample from which the interferents are to be removed is blended with ozonized air and saturated to at least 15% with water vapor. The mixture is then passed through the catalytic reactor which, preferably, contains a mixture of platinum oxide mixed with sand and maintained at an operating temperature of 200° to 280° C. Additional catalytic mixtures which may be employed in the reactor are also disclosed. Methods of preventing the poisoning of catalytic reactors and rejuvenating poisoned catalytic reactors are also disclosed.

2 Claims, 1 Drawing Figure

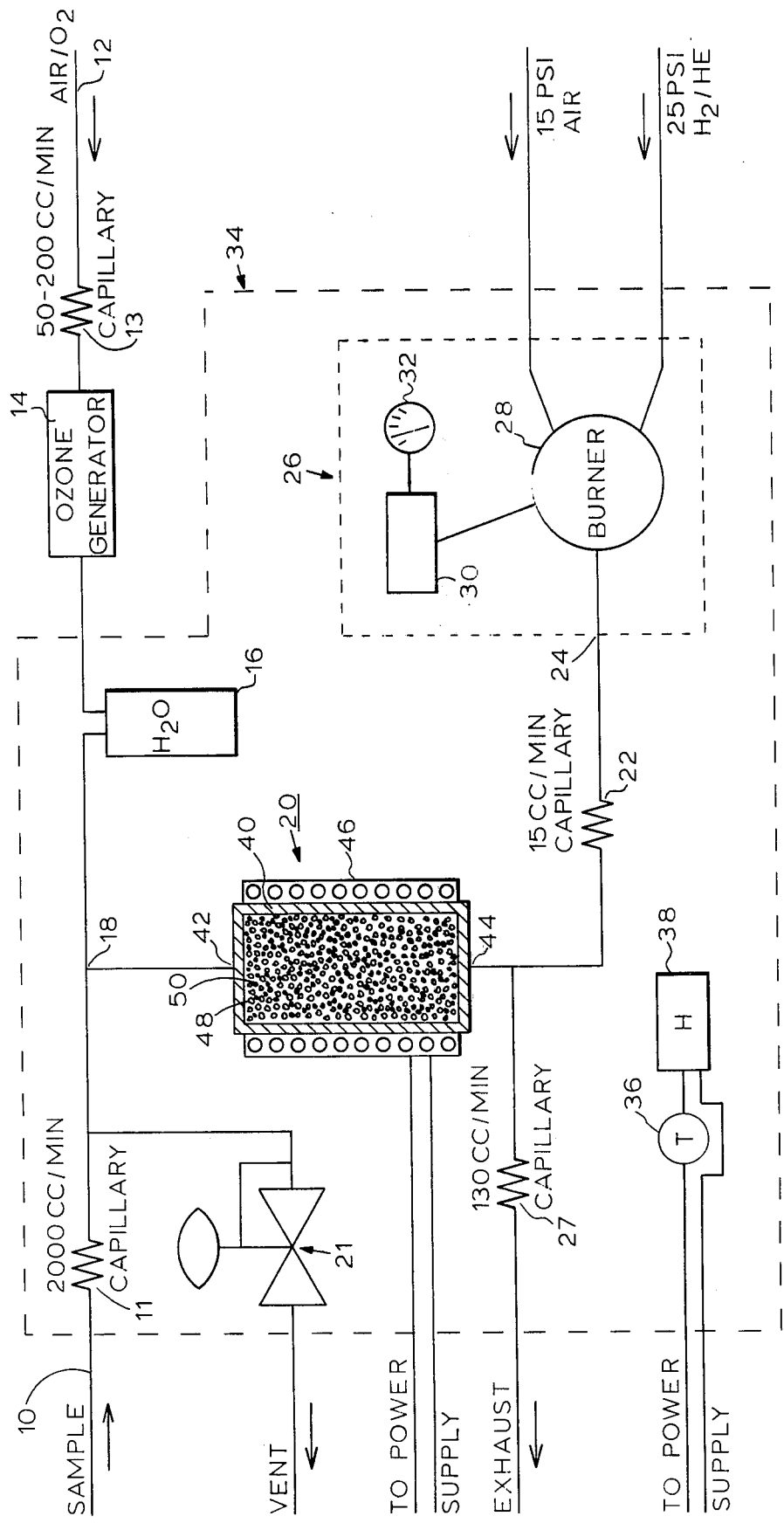

CATALYTIC REACTOR SYSTEMS METHOD AND APPARATUS

BACKGROUND OF THE INVENTION

With increased interest in problems of air pollution, particularly as to pollutants caused by the combustion of hydrocarbons, there has been a rapid increase in research directed to improved gas analysis apparatus. Apparatus for determining the content of a specific component in a gas sample stream is, ideally, designed to be responsive only to the component of interest. Unfortunately, such apparatus often responds not only to the component of interest, but to various interferents as well. Where such interferents exist within the sample stream, they must be removed or their effects masked. Much of the gas being tested is the atmosphere which we breath and the atmosphere often contains numerous hydrocarbons. Various hydrocarbons have become one of the major atmospheric analysis interferent sources. Additionally, hydrocarbons themselves need to be measured in the exhaust emissions of automobiles, in order to improve fuel efficiency and minimize emissions. In particular, in certain testing procedures it is desirable to be able to specifically measure the amount of methane present.

According to guidelines established by the Environmental Protection Agency, methane is the only nonreactive hydrocarbon; all others are considered reactive hydrocarbons. Presently, methane is analyzed either by a gas chromatograph using flame ionization detection, an infrared analyzer, or by selective thermal cracking of other hydrocarbons. Gas chromatographic analysis is not continuous, requires at least one to five minutes for each analysis cycle and is, therefore, not suitable for modal analysis in automobile engine research and development. Infrared analysis, by its very nature, is not selective in spite of the extreme refinements in detectors and optical filters used, as serious interference occurs from other hydrocarbons. Selective thermal cracking is claimed to yield non-quantitative data due to the changing nature of the catalyst.

In a copending application Ser. No. 704,268 by R. M. Neti and R. L. Rogenkamp, entitled "Methane Analyzer", now U.S. Pat. No. 4,063,895 a reactor is disclosed capable of removing the effects of all hydrocarbons from a gas sample stream or all hydrocarbons except methane, to provide apparatus for removing hydrocarbons as interferents from a gas sample stream or, alternatively, to provide the ability to test for methane content as a component of interest in the gas stream. The reactor disclosed therein is capable of removing the effects of a family of interferents from a gas sample stream being used by gas analysis apparatus for the determination of specific components of the gas sample stream. The foregoing apparatus works in a most satisfactory manner for most gas analysis situations such as atmospheric analysis. There are certain limitations, however, when the apparatus is used in gas detection instrumentation employed for the rapid analysis of automobile exhaust emissions directly at or near the tailpipe of the automobile. First, the excessively high hydrocarbon content of the automobile exhaust causes unacceptable variations in the calibratability of the instrument from water vapor over and above that earlier identified and discussed in the aforementioned copending application to Neti et al. Second, while response times of 10 to 15 seconds without electronic enhancement and as low as 3.25 seconds with electronic enhancement possible with such apparatus are superior to the prior art in a rapid testing environment, the requirements of the various testing agencies impose a target response for gas analysis instruments of less than one second.

Thus it is the prime object of the present invention to provide an improved methane analyzer capable of sampling the high hydrocarbon content exhaust gases of an automobile without undue influence from various other interferent hydrocarbons while having the capability of an enhanced response time less than one second.

SUMMARY

The above object is achieved by the apparatus of the present invention wherein in the preferred embodiment air containing oxygen (or pure oxygen, if desired) is passed through an ozone generator to ozonize the oxygen. The ozonized air is then passed through a humidifier maintained at about 70° to 75° C. whereby the ozonized air becomes saturated with water vapor to a 15–16% level. The water saturated, ozonized air is then mixed with the incoming sample and the resultant mixture passed through a catalytic reactor which ideally comprises platinum oxide mixed with sand and maintained at an operating temperature of from 200° to 280° C. After passing through the catalytic reactor, the mixture is passed through a gas analyzer wherein the methane content thereof is detected and displayed.

DESCRIPTION OF THE DRAWING

The single FIGURE is a block diagram of a system according to the present invention for determining the quantity of methane in a sample stream.

DESCRIPTION OF THE PREFERRED EMBODIMENT

The preferred embodiment of a system for detecting the quantity of methane in a sample is shown in the single FIGURE. The sample gas enters input conduit 10 at 5 psi and then passes through capillary 11 which fixes the flow rate at approximately 2,000 cc/minute. Simultaneously, air (or oxygen) enters input conduit 12 at a flow rate of approximately 50 to 200 cc/minute as determined by capillary 13. The air then passes through an ozone generator 14 which causes a portion of the $O_2$ to be converted to $O_3$. The ozonized air then passes from the ozone generator 14 through a humidifier 16 where the water vapor level is raised to about 15%. A preferred embodiment of the humidifier 16 is shown in the aforementioned copending patent application to Neti and Rogenkamp. After passing through the humidifier 16, the now water saturated, ozonized air is blended with a portion of the incoming sample at point 18 from whence the blended mixture enters and passes through a catalytic reactor 20 to be hereinafter discussed in further detail. The balance of the sample is vented to atmosphere through vent means 21. While the preferred embodiment discloses humdifying ozonized air with water vapor in a humidifier and then mixing the humidified/ozonized air with sample, it is to be understood that all that is required is that a mixture of water vapor, ozone, and sample be made which is then passed through reactor 20. Thus, for example, the sample could be humidified and then the humidified sample mixed with ozonized air. After passing through the reactor 20, a portion of the mixture passes through the 15 cc/minute capillary 22 and thence to the input 24 of a gas analyzer generally indicated as 26. The balance of the mixture is exhausted to atmosphere through capillary 27.

In an embodiment tested by applicants, gas analyzer 26 comprises a Beckman Model 400 H$_2$ Flame Ionization Analyzer. In such apparatus, the sample, air, and a mixture of hydrogen and helium, are combined to be burned in a burner 28. Appropriate electronic means 30 detect the ionization which occurs in burner 28 and translate the amount of ionization into an equivalent ppm value which is displayed on meter 32.

In the preferred embodiment of the invention, all the aforementioned apparatus, with the exception of the ozone generator 14, is contained within a housing generally indicated by the dashed area labeled 34 which is maintained at the preferred temperature of 70° to 75° C. by a thermostat 36 and heater 38 to cause the ozonized air to reach and retain a desired water saturation level of approximately 15 to 16% when passing through the humidifier 16 and reactor 20.

The moisture saturation level of the sample was found to be of critical importance to the conducting of a valid analysis on samples of varying humidity and/or non-methane hydrocarbon content. In the removal of interferents from a gas sample to be analyzed for a component of interest, it is acceptable to destroy a portion of the component of interest in the process as long as the amount destroyed is constant and repeatable. Compensation can be made for such constant and repeatable destruction of the component of interest. For example, if 50% is destroyed, the final answer is merely doubled to ascertain the quantity in the original sample stream. Methane is partially oxidized to CO$_2$ and H$_2$O when passed through the catalytic reactor 20. This conversion, it was discovered, is not constant and repeatable as necessary but, rather, is strongly influenced by the humidity of the sample. This is true whether the methane gas is alone or in a mixture containing other hydrocarbons along with a carrier gas such as N$_2$. Moreover, if other hydrocarbons are, in fact, actually present in the sample in substantial quantities, then the water formed from their combustion products in the reactor acts with the original water content of the sample to decrease the loss of methane when the methane is passed through the reactor 20. Thus, with varying amounts of moisture and/or other hydrocarbons present in the sample along with the methane of interest, a non-constant partial oxidation of the methane is effected. Being non-constant, it cannot be compensated for in the analyzer 26 in the manner described above. It was found that by humidifying both the sample and the known content span gases (used to adjust the span of the analyzer 26 in the standard manner) to the 15-16% saturation level, the maximum anticipated level of hydrocarbons and moisture no longer yield spurious results. That is, a constant, reproducible reduction in the methane present is effected which, in turn, can be compensated for in the gas analyzer 26.

A quartz lamp reactor such as that described in the aforementioned copending application to Neti and Rogenkamp could be employed as reactor 20. The system as heretofore described, if used in conjunction with a quartz lamp reactor, would be capable of sampling the high hydrocarbon exhaust gases set forth as one objective of the invention. The second objective of providing an enhanced response time in the less than one second region, however, would not be met. Accordingly, in the preferred embodiment, reactor 20 is a catalytic reactor comprising a housing containing platinum oxide catalyst mixed with sand and maintained at an operating temperature of 200° to 280° C. In attempting to produce a system having the attributes desired, a number of other catalytic mixtures were tried. All of the following were found to be useful to a fairly acceptable degree:

| | Material | Temperature ° C |
|---|---|---|
| 1. | Vitreous carbon | 500-650 |
| 2. | Vitreous carbon and cupric oxide | 500-600 |
| 3. | Cupric oxide | 450-600 |
| 4. | Cobalt oxide | 450-600 |
| 5. | Palladium on alumina | 200-260 |
| 6. | Platinum black mixed with Teflon powder | 200-350 |
| 7. | Platinum black mixed with sand | 200-350 |
| 8. | Palladium oxide mixed with sand | 200-350 |

Of all the catalysts, however, the aforementioned platinum oxide supported on a substrate of sand and maintained at an operating temperature of 200°-280° C. was found to provide superior results.

Referring once again to the FIGURE, reactor 20, in its preferred embodiment, consists of a closed cylindrical body 40 having an inlet conduit 42 on one end and an outlet conduit 44 on the other end. Heating means 46 are disposed in thermal relationship to body 40 and connected to an appropriate supply of power whereby body 40 can be maintained at the desired operating temperature of the reactor. In the preferred embodiment, the heater is set to maintain the reactor at an operating temperature of 250°-260° C. The catalyzing mixture contained within the reactor body 40 comprises a mixture of platinum oxide powder and sand. A tested embodiment of the applicants comprised one gram of 250-300 mesh platinum oxide on 40 grams of sand of 30-120 mesh. The sand acts as a substrate to support the platinum oxide which is the actual catalyst. The mixture can be formulated by pouring the platinum oxide powder and sand into a container and shaking. In so doing, a glass container should be employed as applicants found that plastic containers will generate sufficient static electricity to maintain the platinum oxide powder in contact with the container so that satisfactory mixing of a homogenous mixture of platinum oxide and sand, as desired, will not occur.

The aforementioned system was found to provide response times of as short as 2.2 seconds without enhancing electronics. From past experience, it is anticipated that response times as low as 0.5 second can be obtained by employing the proper enhancement electronics in conjunction therewith. When employing a gas analysis system according to the present invention, methane content of an automobile exhaust up to 1600 ppm's could be analyzed successfully. Interference effects by components in the sample stream were found to be:

Ethane <5%
Propane and Higher Aliphatics <1%
Ethylene, Acetylene and Unsaturates <1%
Aromatics, Benzene, etc. <1%

In addition to the specific method and apparatus hereinbefore described in relation to the analysis of a sample gas stream for methane content, the present invention includes two aspects which will now be addressed with particularity.

Most catalytic systems are subject to poisoning by such compounds as CO, H$_2$S, X$_2$ and metals such as Pb, Hg, etc. As a prime example, the gasoline and automotive industries were forced into developing non-leaded fuels and engines that would run with such fuels because of the necessary of incorporating catalytic converters subject to poisoning by the lead in leaded fuel in automobile exhaust systems in order to meet air pollution standards. Of particular importance in the analysis of automotive exhaust gases, CO is a serious poisoning threat to systems using catalytic reactors such as that employed in the present invention. In the present invention, however, the poisoning of the catalyst from CO in the exhaust gases has been eliminated by the inclusion of ozone within the sample stream. It was found that including ozone keeps the catalyst in the oxidized condition thereby preventing poisoning. This has been demonstrated by actually operating a system according to the present invention over extended periods analyzing exhaust gases with a high CO content without loss of system performance.

In addition to the poisoning prevention aspects of the present invention, and perhaps even more important, it was found that once a catalytic reactor had been poisoned it could be rejuvenated to an acceptable operating condition by passing a continuous stream of ozone through it while heating it at its normal operating temperature. As to CO poisoning in particular, this too was demonstrated with an actual system according to the present invention built and tested by applicants.

It is to be noted that the rejuvenation process is not instantaneous. The catalyst of the catalytic reactor reactivates over a period of hours and not minutes. Considering the cost of most noble metal catalytic converters or reactors, however, the time is well worth spending.

While the specific rejuvenation of an automotive catalytic converter poisoned by the use of leaded gasoline was not undertaken, it is applicants' belief (with no evidence to the contrary) that the same process of passing ozone through the catalytic converter heated to its operating temperature for an extended period of time would be successful in restoring the converter to within specifications. It follows, that the injection of ozone into the exhaust gases of an automobile or other internal combustion engine apparatus prior to a catalytic converter would prevent the eventual poisoning of the converter so as to make at least the catalyst itself virtually good for life. Flow rates of the ozone would, of course, have to be scaled up to account to the greater size of the automotive catalytic converter.

While various specific alternate catalytic mixtures have been disclosed herein and the preferred catalytic mixture of platinum oxide on sand identified, it is to be understood that other oxides such as cupric, manganese, etc., are also suitable either alone or in mixtures thereof with platinum or palladium on a suitable substrate material to realize the benefits of the present invention to a lesser degree. It is to be understood as well that where the humidity of the sample is known to be of a humidity level of at least 15–16% in the case of gas analysis of the sample, further humidification is unnecessary so that humidifier 16 may be eliminated. Similarly, where the gas stream is passed through the catalytic reactor or converter only to remove undesired components, such as in the case of the automotive exhaust catalytic converter, and no subsequent analysis is to be made, the humidifier 16 is not necessary.

Having thus described our invention, we claim:

1. An improved methane analyzer comprising:
    (a) a source of ozone;
    (b) mixing means for mixing a sample containing methane and other hydrocarbons with ozone, said mixing means having a pair of inlets and an outlet, one of said inlets adapted to receive a sample to be analyzed, the other of said pair of inlets being connected to said source of ozone;
    (c) a catalytic reactor for removing hydrocarbons other than methane and having an inlet and an outlet, said inlet being connected to said outlet of said mixing means;
    (d) means for humidifying connected to cause water vapor to be included in the sample/ozone mixture input to said reactor;
    (e) means for detecting and displaying the quantity of methane in a sample having an inlet and an outlet, said inlet being connected to said outlet of said reactor to receive humidified, ozonized and reacted sample therefrom;
    (f) an enclosure having at least said mixing means, said humidifying means, and said reactor disposed therein; and,
    (g) heating means for maintaining said enclosure at an internal temperature of 70° to 75° C.

2. An improved methane analyzer as claimed in claim 1 wherein said reactor contains platinum oxide supported in a substrate of sand and additionally comprising:
    means for heating said reactor to and maintaining said reactor at an operating temperature of 200° to 280° C.

* * * * *